United States Patent
Watson et al.

(10) Patent No.: US 6,429,434 B1
(45) Date of Patent: Aug. 6, 2002

(54) TRANSMISSION ATTENUATION CORRECTION METHOD FOR PET AND SPECT

(76) Inventors: Charles C. Watson, 12816 Peachview Dr.; Stephen D. Miller, 11920 Butternut La.; Ronald Nutt, 2121 Lake Point Dr., all of Knoxville, TN (US) 37922; Michael E. Casey, 7011 Sherwood Dr., Knoxville, TN (US) 37919; James J. Hamill, 7909-B Bennington Dr., Knoxville, TN (US) 37909

( * ) Notice: Subject to any disclaimer, the term of this patent is extended or adjusted under 35 U.S.C. 154(b) by 0 days.

(21) Appl. No.: 09/398,497

(22) Filed: Sep. 17, 1999

Related U.S. Application Data (63) Continuation-in-part of application No. 09/070,951, filed on May 1, 1998.

(51) Int. Cl.$^7$ ............................................. G01T 1/166
(52) U.S. Cl. ............................... 250/363.04; 250/370.09
(58) Field of Search ...................... 250/363.04, 363.03, 250/370.09, 370.1; 378/4

(56) References Cited

U.S. PATENT DOCUMENTS 4,135,096 A * 1/1979 Giordano (List continued on next page.)

FOREIGN PATENT DOCUMENTS

| JP | 59-99377 A | * | 6/1984 |
| JP | 61-235782 A | * | 10/1996 |

OTHER PUBLICATIONS

Bailey D.L., Hutton B.F., Walker, P.J., Improved SPECT Using Simultaneous Emission and Transmission Tomography, Journal of Nuclear Medicine, vol. 28, No. 5, May 1987.

(List continued on next page.)

Primary Examiner—David P. Porta
Assistant Examiner—Pamela R. Hobden
(74) Attorney, Agent, or Firm—Pitts & Brittian, P.C.

(57) ABSTRACT

A transmission source serves to detect activity from a radiation source for correcting attenuation in either PET mode or SPECT mode. The transmission source includes a detector dedicated to collecting attenuation data in PET mode. A collimated radiation source and a detector are positioned with respect to a tomography device such that only a selected strip of the imaging detector of the tomograph is illuminated such that events unrelated to the attenuation are eliminated. The transmission source can either be a coincidence transmission source or a singles transmission source and includes a collimator in which is disposed a radiation source. An opening is defined by the collimator for exposing a selected portion of the imaging detectors of the tomograph device. Positioned behind the radiation source, relative to the imaging detectors, is the dedicated attenuation detector. In a dual head tomograph device, one transmission source of the present invention is disposed opposite each bank of imaging detectors. The sources and the associated collimators are positioned to the side of each head at a slight angle relative to the respective head. The sources and detectors are fixed relative to the imaging heads. In order to obtain full coverage of the field of view (FOV) in the same manner as for an emission scan, the heads and sources are rotated about the center of the camera. In SPECT mode, the point source is selected to have sufficiently high energy to shine through the patient and the collimators associated with the imaging detector.

27 Claims, 10 Drawing Sheets

U.S. PATENT DOCUMENTS

| | | | |
|---|---|---|---|
| 4,743,764 A | | 5/1988 | Casey |
| 5,338,936 A | | 8/1994 | Gullberg et al. |
| 5,430,297 A | | 7/1995 | Hawman |
| 5,434,416 A | | 7/1995 | Motomura et al. |
| 5,479,021 A | | 12/1995 | Morgan et al. |
| 5,608,221 A | | 3/1997 | Bertelsen et al. |
| 5,638,817 A | * | 6/1997 | Morgan et al. .......... 128/653.1 |
| 5,650,625 A | | 7/1997 | Stoub |
| 5,728,361 A | * | 3/1998 | Holley .................... 423/449.6 |
| 6,008,493 A | * | 12/1999 | Shao et al. ............ 250/363.04 |
| 6,201,247 B1 | * | 3/2001 | Lutheran et al. ....... 250/363.04 |
| 6,236,050 B1 | * | 5/2001 | Tumer ................... 250/370.09 |
| 6,236,051 B1 | * | 5/2001 | Yamakawa et al. ...... 250/370.1 |

OTHER PUBLICATIONS

Lange K., Bahn M., Little R., A Theoretical Study of Some Maximum Likelihood Algorithms for Emission and Transmission Tomography, IEEE Log No. 8714498, 1987.

Gullberg G.T., Huesman R.H., Malko R.A., Plec N.J., Budinger T.F., An Attenuated Projector–Backprojector for Iterative SPECT Reconstruction, Physics in Medicine and Biology, vol. 30, No. 8, 799–816, 1985.

Chang L.T., A Method for Attenuation Correction in Radionuclide Computed Tomography, IEEE Transactions for Nuclear Science, vol. NS–25, Feb. 1, 1978.

Hudson H.M., Larkin R.S., Accelerated Image Reconstruction Using Ordered Subsets of Projection Data, IEEE Transactions on Medical Imaging, vol. 13, No. 4, Dec. 1994.

R.D. Evans: "The Atomic Nucleus", Kreiger, 1955.

J.C. Moyers: "A High Performance Detector Electronics System for Positron Emission Tomography", Masters Thesis, University of Tennessee, Knoxville, TN, 1990.

R.A. DeKemp, et al.: "Attenuation Correction in PET Using Single Photon Transmission Measurement" Masters Thesis University of Tennessee, Knoxville, TN, 1992.

S.R. Cherry, et al.: "3–D PET Using a Conventional Multislice Tomograph Without Septa", Jl. C. A. T., 15(4) 655–668.

J.S. Karp, et al.: "Singles Transmission in Volume–Imaging PET With a $^{137}$Cs Source", Phys. Med. Biol. vol. 40, 929–944 (1995).

S.K. Yu, et al.: "Single–Photon Transmission Measurements in Positron Tomography Using $^{137}$Cs", Phys. Med. Biol. vol. 40, 1255–1266 (1995).

S.R. Cherry, et al.: "Optical Fiber Readout of Scintillator Arrays using a Multi–Channel PMT: A High Resolution PET Detector for Animal Imaging", IEEE Transactions on Nuclear Science, vol. 43, No. 3, 1932–1937 (Jun. 1996).

J.A. McIntyre, et al.: "Construction of a Positron Emission Tomograph with 2.4 mm Detectors", IEEE Transactions on Nuclear Science, vol. 33, No. 1, 425–427 (Feb., 1986).

* cited by examiner

TRANSMISSION ATTENUATION CORRECTION METHOD FOR PET AND SPECT

This application in part discloses and claims subject matter disclosed in our earlier filed pending application, Ser. No. 09/070,951, filed on May 1, 1998.

TECHNICAL FIELD

This invention relates to the field of tomography. More specifically, the present invention relates to a method of measuring and correcting the attenuation associated with detecting coincidences using a collimated source and a dedicated detector for improved measurement sensitivity.

BACKGROUND ART

Positron Emission Tomography (PET) has gained significant popularity in nuclear medicine because of the ability to non-invasively study physiological processes within the body. Applications employing the PET technology for its sensitivity and accuracy include those in the fields of oncology, cardiology and neurology.

Using compounds such as $^{11}$C-labeled glucose, $^{18}$F-labeled glucose, $^{13}$N-labeled ammonia and $^{15}$O-labeled water, PET can be used to study such physiological phenomena as blood flow, tissue viability, and in vivo brain neuron activity. Positrons emitted by these neutron deficient compounds interact with free electrons in the body area of interest, resulting in the annihilation of the positron. This annihilation yields the simultaneous emission of a pair of photons (gamma rays) approximately 180° (angular) apart. A compound having the desired physiological effect is administered to the patient, and the radiation resulting from annihilation is detected by a PET tomograph. After acquiring these annihilation "event pairs" for a period of time, the isotope distribution in a cross section of the body can be reconstructed.

PET data acquisition occurs by detection of both photons emitted from the annihilation of the positron in a coincidence scheme. Due to the approximate 180° angle of departure from the annihilation site, the location of the two detectors registering the "event" define a chord passing through the location of the annihilation. By histogramming these lines of response (the chords), a "sinogram" is produced that may be used by a process of back-projection to produce a three dimensional image of the activity. Detection of these lines of activity is performed by a coincidence detection scheme. A valid event line is registered if both photons of an annihilation are detected within a coincidence window of time. Coincidence detection methods ensure (disregarding other second-order effects) that an event line is histogrammed only if both photons originate from the same positron annihilation.

In the traditional (2-D) acquisition of a modern PET tomograph, a collimator (usually tungsten) known as a septa is placed between the object within the field-of-view and the discrete axial rings of detectors. This septa limits the axial angle at which a gamma ray can impinge on a detector, typically limiting the number of axial rings of detectors that a given detector in a specific ring can form a coincidence with to a few rings toward the front of the tomograph from the given detector's ring, the same ring that the detector is within, and a few rings toward the rear of the tomograph from the given detector's ring.

The current state of the art nuclear medicine camera is capable of operating in either PET or Single Photon Emission Computed Tomography, ("SPECT"), modes. Fundamentally, in both modes, gamma photons emitted from within a patient are detected. However, a significant portion of these emitted photons are obstructed from reaching the detectors by colliding with atoms. When this occurs, one significant possibility is a course alteration away from the detector that may result in a missed detection. The degree of attenuation depends upon the amount and density of matter between the emitting source and the detector, and will vary from subject to subject. The more attenuation present, the less probable will be the accurate detection of a gamma photon. Unless the amount of attenuation is known, the detected activity within a defined energy window underestimates the true activity. This results in poorer contrast and attenuation artifacts in the reconstructed images. Conditions such as these reduce the confidence one may have in extracting information for diagnosis. However, attenuation methods well suited for SPECT are poorly suited for PET.

To compensate for this phenomenon, it is now common to incorporate an apparatus to transmit gamma photons of a known flux density through a patient so that the patient induced attenuation can be measured. Attenuation was first measured in PET by using a ring of positron emitting isotope surrounding the object to be measured. In this technique, the ratio between a transmission scan and a blank scan form the attenuation. The blank is measured by simply measuring the rate that gamma rays from positrons are detected by the detection system when no attenuating media is present. In the original scanners as described above as having septa, the septa are provided for collimating the gamma rays in an axial direction, but the rings allow for no transaxial collimation. The lack of collimation allow the acceptance of scattered events into the transmission measurement, resulting in an underestimate of the attenuation. To improve the transmission measurement, systems use rotating rod sources. These sources are disposed in parallel fashion to the axis of the scanner and are collimated in the axial direction by the septa. In the transaxial direction, the collimation may be provided electronically since the position of the source is known. However, the activity in the rod must be the same as that activity in the earlier ring source to provide the same count rate. With modern block detectors, the dead-time of the near block limits the activity in the rod.

A more recent advancement in PET acquisition is 3-D, in which the septa are removed, which allows a given detector to be in coincidence with detectors from all other detector rings. With the advent of three-dimensional reconstruction techniques, greater sensitivity to emission counts is possible if the septa are removed. As the septa represent a significant cost, there is also an economic incentive to exclude them from the system. However, with the absence of septa, the problems of both detector dead-time and scatter are magnified.

Since the position of a source with respect to the detector system can be known, there is no need to detect coincidences, thereby allowing the use of a source that emits single gamma rays. Only one detector—the detector on the far side of the system—is needed to make the transmission or blank measurements. Without the counting losses due to the dead-time of the near detector, the activity of the source may be increased resulting in an increase in count-rate and thus a better quality measurement. However, without axial collimation, the scatter included in the transmission scan causes an underestimate of the attenuation measurement. To decrease the possibility of scatter, the gamma rays from the source can be collimated with lead or tungsten to form a beam that illuminates only a narrow plane of detectors.

Other gamma rays that would only contribute to background are eliminated. Since the directionality of single gamma rays cannot be determined, only a single point of activity illuminating a detector bank can be used. This requires increased levels of activity to meet the count-rate needed for an adequate quality measurement. Also, the scanning protocol is more efficient if the transmission measurement is performed after the patient has been injected with radioactivity. Even though a different isotope such as $^{137}$Cs which emits gamma rays with an energy of 662 keV can be used for the transmission scan, there is a significant difficulty in distinguishing the transmission events from the emission events.

(SPECT) is similar to PET. However, in SPECT, only a single photon from a nuclear decay within the patient is detected. Also, the line of response traveled by the photon is determined exclusively by detector collimation in SPECT, as opposed to the coincident detection of two collinear photons as in PET.

There are a number of correction methods in the art. However, these methods utilize SPECT based approaches for transmission based attenuation correction that is not well suited to PET. Typical of the art are the following:

| Pat. No.   | Inventor(s)      | Issue Date       |
|------------|------------------|------------------|
| 5,338,936  | Gullberg et al.  | Aug. 16, 1994    |
| 5,430,297  | Hawman           | July 4, 1995     |
| 5,434,416  | Mototmura et al. | July 18, 1995    |
| 5,479,021  | Morgan et al.    | Dec. 26, 1995    |
| 5,608,221  | Bertelsen et al. | March 4, 1997    |
| 5,650,625  | Stoub            | July 22, 1997    |

Also typical of the art are the following:

Tan P., Bailey D. L., Meikle S. R., Eberl S. Fulton R. R., and Hutton B. F., *A Scanning Line Source for Simultaneous Emission and Transmission Measurements in SPECT*, Journal of Nuclear Medicine, col. 34, No. 10, October 1993.

Lange K., Carson R., *EM Reconstruction Algorithms for Emission and Transmission Tomography*, Journal of Computer Assisted Tomography, Vol & No. 2, 1984.

Bailey D. L., Hutton B. F., Walker P. J., *Improved SPECT Using Simultaneous Emission and Transmission Tomography*, Journal of Nuclear Medicine, Vol. 28, No. 5, May 1987.

Lange K., Bahn M., Little R., *A Theoretical Study of Some Maximum Likelihood Algorithms for Emission and Transmission Tomography*, IEEE Log Number 8714498, 1987.

Gullberg G. T., Huesman R. H., Malko R. A., Plec N. J., Budinger T. F., *An Attenuated Proiector-Backprojector for Iterative SPECT Reconstruction*, Physics in Medicine and Biology, Vol. 30, No. 8, 799–816, 1985.

Chang L. T., *A Method for Attenuation Correction in Radionuclide Computed Tomography*, IEEE Transactions for Nuclear Science, Vol. NS-25, No. 1, February 1978.

Hudson H. M., Larkin R. S., *Accelerated Image Reconstruction Using Ordered Subsets of Projection Data*, IEEE Transactions on Medical Imaging, Vol. 13, No. 4, December 1994.

Hollinger D. F., Loncaric S., Yu D. C., Ali A., Chang W., *Using Fast Sequential Asymetric Fanbeam Transmission CT for Attenuation Correction of Cardiac SPECT Imaging*, Journal of Nuclear Medicine, 1998; 39:1335–1344.

Kak A. C., Slaney M., *Principles of Computerized Tomographic Imaging*, IEEE Press 1987 ISBN 0-7803-0447-0.

Sorenson J. A., Phelps M. E., *Physics in Nuclear Medicine*, Second Edition, Grune & Stratton, Inc. Harcourt, Brace Jovanovich, 1987, ISBN 0-8089-1804-4.

The details of carrying out a PET study are given in numerous publications. Typically, the following references provide a background for PET. These are incorporated herein by reference for any of their teachings.

1. M. E. Phelps, et al.: "Positron Emission Tomography and Audiography", Raven Press, 1986;
2. R. D. Evans: "The Atomic Nucleus", Kreiger, 1955;
3. J. C. Moyers: "A High Performance Detector Electronics System for Positron Emission Tomography", Masters Thesis, University of Tennessee, Knoxville, Tenn., 1990;
4. U.S. Pat. No. 4,743,764 issued to M. E. Casey, et al, on May 10, 1988;
5. R. A. DeKemp, et al.: "Attenuation Correction in PET Using Single Photon Transmission Measurement", Med. Phys., vol. 21, 771–8, 1994;
6. S. R. Cherry, et al.: "3-D PET Using a Conventional Multislice Tomograph Without Septa", JI. C. A. T., 15(4) 655–668.
7. J. S. Karp, et al.: "Singles Transmission in Volume-Imaging PET With a $^{137}$Cs Source", Phys. Med. Biol. Vol. 40, 929–944 (1995).
8. S. K. Yu, et al.: "Single-Photon Transmission Measurements in Positron Tomography Using $^{137}$Cs", Phys. Med. Biol. Vol. 40, 1255–1266 (1995).
9. G. F. Knoll: *Radiation Detection and Measurement*, John Wiley & Sons (1989).
10. S. R. Cherry, et al.: "Optical Fiber Readout of Scintillator Arrays using a Multi-Channel PMT: A High Resolution PET Detector for Animal Imaging",. IEEE Transactions on Nuclear Science, Vol. 43, No. 3, 1932–1937 (June, 1996).
11. J. A. McIntyre, et al.: "Construction of a Positron Emission Tomograph with 2.4 mm Detectors", IEEE Transactions on Nuclear Science, Vol. 33, No. 1,425–427 (February, 1986).

Both PET and SPECT systems are also well known to persons skilled in the art.

In order to achieve maximal quantitative measurement accuracy in tomography applications, an attenuation correction must be applied to the collected emission data. In a PET system, for example, this attenuation is dependent on both the total distance the two gamma rays must travel before striking the detector, and the density of the attenuating media in the path of travel. Depending on the location of the line of response within. the patient's body, large variations in attenuating media cross section and density have to be traversed. If not corrected for, this attenuation causes unwanted spatial variations in the images that degrade the desired accuracy. As an example, for a cardiac study the attenuation is highest in the line of responses (LORs) passing through the width of the torso and arms, and attenuation is lowest in the LORs passing through from the front to the back of the chest.

Typically, the attenuation correction data in PET systems is produced by either: shape fitting and linear calculations using known attenuation constants, these being applicable to symmetric well-defined shapes such as the head and torso below the thorax (calculated attenuation); or through the measurement of the annihilation photon path's attenuation using a separate transmission scan (measured attenuation). The use of calculated attenuation correction, which introduces no statistical noise into the emission data, can be automated for simple geometries such as the head, and is the most prominent method used for brain studies. However, complexities in the attenuation media geometry within the chest have prevented the application of calculated attenuation from being practical for studies within this region of the body. Accordingly, transmission scanning has been utilized.

The total attenuation of a beam along a LOR through an object is equal to the attenuation that occurs for the two photons from an annihilation. Thus, the emission attenuation along the path can be measured by placing a source of gamma rays on the LOR outside of the body and measuring attenuation through the body along this line. It has been the practice to accomplish this attenuation measurement by placing a cylindrical positron emitter "sheet" within the PET tomograph's field of view (FOV) but outside of the region (the object) to be measured. The ratio of an already acquired blank scan (no object in the FOV) to the acquired transmission scan is calculated. These data represent the desired measured attenuation factors, which may vary spatially. These data are then applied to the emission data after a transmission scan of the object to correct for the spatial variations in attenuation.

There are two types of transmitter source units conventionally utilized in PET transmission scan data collection, both of which form a "sheet" of activity to surround the patient. One involves the placement of rings of activity aligned with detector rings around the inner face of the septa. The second type utilizes the rotation of one or more axially-oriented rods of activity in a circular path just inside the inner face of the septa.

The first of these two emitter systems (the ring source method) significantly reduces the sensitivity of the tomograph due to the close source-proximity dead time effects of the source activity on all of the detectors. Further, removal of this assembly is either performed manually by facility personnel or by a complex automated mechanical assembly. Large, cumbersome, out of the FOV shielding is required for storage of the automated source when not in use, adding to the depth of the tomograph tunnel and, thus increasing incidence of patient claustrophobia. The second type of emitter, using rotating source(s) suffers from the above-mentioned problems and also, due to the shielding requirements, reduces the patient tunnel diameter, further increasing patient claustrophobia symptoms.

Both of the above automated source transportation methods suffer from high mechanical component cost and from low sensitivity. Due to the dead-time-induced reduction in tomograph sensitivity, lengthy acquisitions are required in order to achieve usable low noise transmission scan data.

In order to reduce costs in scintillator detector applications, multiplexing techniques based on the use of fiber optics are advantageous. Those disclosures made by Cherry, et al. (Cherry), and McIntyre, et al. (McIntyre), teach the use of fiber optics connected between the imaging detectors and multichannel photomultipliers (PMT's). Cherry discloses the use of a multi-channel PMT in association with an 8×8 array of bismuth germanate (BGO) crystals. As discussed by Cherry, a charge division readout board is used to convert the 64 signals into four position sensitive signals which determine the crystal interaction. In the earlier McIntyre article, the authors disclose the use of fiber optics coupled between the detectors and a number of multi-channel PMT's. Specifically, McIntyre teaches the use of 288 PMT's in association with 8,192 detectors, for reducing the number of required PMT's by a factor of about 28.4.

In the McIntyre embodiment, eight detector rings are each divided into four quadrants. Each ring is comprised of sixteen concentric rings. The respective quadrants for the eight detector rings are grouped together for a total of 256 detectors per quadrant group. Sixteen "coarse" fiber sets connect sixteen PMT's to the 256 detectors, with sixteen detectors in one ring quadrant connected to one PMT. Similarly, sixteen "fine" fiber sets connect sixteen PMT's to the 256 detectors, with corresponding detectors in each ring quadrant of a quadrant group being connected to one PMT. One PMT is connected to each ring quadrant. Thus, a total of 32 PMT's are required for determining the particular detector "Θ" address within a quadrant. Similarly, 32 PMT's are required to determine the "r" address, corresponding to which of the concentric rings in a particular ring the detector is disposed. Finally, eight PMT's are required to determine which ring quadrant the detector is disposed. Thus, a total of 72 PMT's are required for each quadrant for a total of 288 PMT's in association with 8,192 detectors.

Therefore, it is an object of the present invention to provide a system for detecting coincident activity from a point source.

Another object of the present invention is to provide such a system which includes a detector dedicated to collecting attenuation data.

Yet another object of the present invention is to provide a system for detecting coincident activity while illuminating only a strip of the imaging detector in order to eliminate events not of interest in the attenuation measurement.

A further object of the present invention is to provide a collimated point source and dedicated detector whereby only a selected strip of the imaging detector is illuminated such that events unrelated to the attenuation are eliminated.

Still another object of the present invention is to provide an arrangement whereby gamma radiation detected by dedicated detectors is transmitted to a plurality of PMT's such that an address of each gamma radiation detector is readily determined and such that the total required number of PMT's is reduced relative to conventional devices.

A further object of the present invention is to provide a single method for acquiring patient attenuation measurements on a dual modality PET/SPECT camera.

A still further object of the present invention is to provide a transmission source capable of "shining through" the patient and the collimator.

It is yet another object of the present invention to provide a method and a device in which transmission data emission data can be acquired either simultaneously, gated sequential in which emission data then transmission data are acquired at each gantry angle, or sequentially in which a transmission scan is performed either before or after a complete emission subject study is collected.

A further object of the present invention is to provide a method and device in which the placement of the transmission source will allow a continuous range of angles between the source and the opposed detector ranging from 90 to 180 degrees.

Other objects and advantages of the present invention will become more apparent upon review of the detailed description and associated drawings of the scintillator detector array for encoding the energy, position and time coordinates of gamma-ray interactions.

DISCLOSURE OF THE INVENTION

Other objects and advantages will be accomplished by the present invention which serves to detect activity from a, preferably, collimated point source. The present invention includes a detector dedicated to collecting attenuation data. The collimated point source and dedicated detector are positioned with respect to the tomography device such that only a selected strip of the imaging detector is illuminated such that events unrelated to the attenuation are eliminated.

The source of the present invention includes a collimator in which is disposed a point source. An opening is defined by the collimator for exposing a selected portion of the imaging detectors of the tomograph device. Positioned behind the point source, relative to the imaging detectors, is an attenuation detector dedicated to collecting attenuation data. Because the attenuation detector is dedicated to the attenuation measurement, the requirements for the attenuation detector are different from those for the imaging detector. For instance, it is not required that the attenuation detector be able to accurately determine the energy or spatial position of events within the detector, as is necessary for standard imaging detectors. It is therefore possible to design such an attenuation detector with much less dead time, and much higher count rate performance, than a standard imaging detector. The improved count rate performance of the attenuation detector enables significant reduction of statistical noise in the attenuation correction measurement. The attenuation detector and collimator are designed to illuminate only a strip of the imaging detector, and the corresponding aperture of the attenuation detector, thereby eliminating events not of interest in the attenuation measurement. This also reduces dead time of the system and improves the count rate performance for events of interest.

A source of the present invention is disposed opposite each bank of imaging detectors of a dual head camera. Each source contains four point sources arranged along the axial extent. The sources and the associated collimators are positioned to the side of each head at a slight angle relative to the respective head. The sources and detectors are fixed relative to the imaging heads. In order to obtain full coverage of the field of view (FOV) in the same manner as for an emission scan, the heads and sources are rotated about the center of the camera.

The present invention further provides an arrangement of fiber optics interconnected between a plurality of dedicated gamma radiation detectors and a lesser number of photomultiplier tubes. The gamma radiation detectors are each provided for dedicated detection of 511 keV gamma radiation from one of a plurality of point sources disposed in a collimator. The arrangement of fiber optics is designed such that the address of a particular gamma radiation detector is readily discernable while minimizing the number of PMT's required to process data accumulated by the gamma radiation detectors.

An alternate embodiment is described that allows provide a single method for acquiring patient attenuation measurements on a dual modality PET/SPECT camera. As recognized by those skilled in the art, dual purpose PET/SPECT cameras typically consist of two or more rectangular detectors. As described above, a collimated point source and dedicated detector are positioned with respect to the tomography device such that only a selected strip of the imaging detector is illuminated such that events unrelated to the attenuation are eliminated. Since state of the art SPECT requires a collimator in front of the detector, due to the current state of the art in gamma photon detection, the offset transmission source will likely not be in the direct FOV of the collimator. This results in attenuation to various degrees of the transmission beam (flux) due to the collimator. To overcome this problem, in the alternate embodiment, the point source is selected to have a sufficiently high energy and flux density to "shine through" the subject and additionally, the collimator.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

A transmission source incorporating various features of the present invention is illustrated generally at 10 in the figures. The transmission source, or device 10, is designed for collimating and detecting activity from a source 12 of radiation such as the illustrated point source 12. Moreover, the device 10 of the present invention includes a detector 18 dedicated to collecting attenuation data. The collimated point source 12 and dedicated attenuation detector 18 are positioned with respect to the tomography device 22 such that only a selected strip of the imaging detector 14 is illuminated such that events unrelated to the attenuation are eliminated. The imaging detector 14 may be comprised of either a plurality of imaging detectors 14 or a single continuous imaging detector 14 having spatial positioning capabilities.

As will be discussed throughout, many variations of the present invention may be adapted to fit various conventional applications of tomography. For example, the device 10 of the present invention may be adapted to various conventions of PET, SPECT, simultaneous PET/SPECT, and other tomography applications or combinations thereof. The radiation source 12 may define various configurations, as will be discussed below, as required. Further, the radiation source 12 may be maintained stationary with respect to either or both of the dedicated attenuation detector 18 and the imaging detector 14, or may be moved to various positions within the tomograph device for individually collecting attenuation data corresponding to more than one imaging detector 14. In the latter case, the path in which the radiation source 12 is moved may be in any conventional path, or any path yet to be employed.

Figure 1:
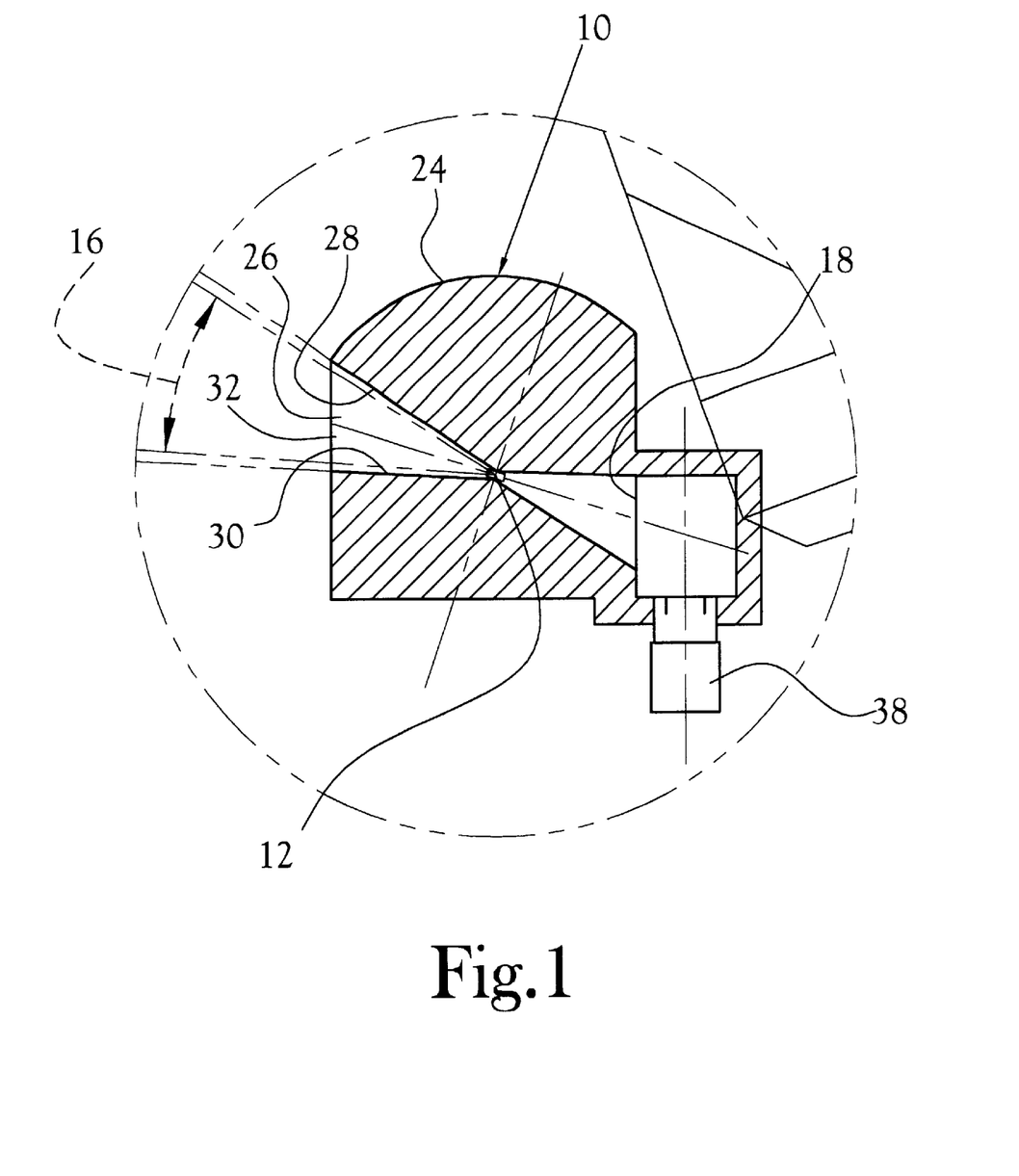
FIG. 1 is an end elevation view, in section, of the transmission source constructed in accordance with several features of the present invention showing a collimated point source and a dedicated detector.

The device 10 of the present invention includes a source collimator 24 in which is disposed a point source 12. An opening 26 is defined by the source collimator 24 for exposing a selected portion of the imaging detectors 14 of the tomograph device 22. To this extent, the opening 26 defines a top and a bottom shield wall 28,30, with the top shield wall 28 extending from the point source 12 toward the far detector 44 of the imaging detectors 14 opposite the device 10, and the bottom shield wall 30 extending toward the near detector 46 of the imaging detectors 14. Side shield walls 32 are defined to limit the width of the collimated radiation beam. Positioned behind the point source 12, relative to the imaging detectors 14, is an attenuation detector 18 dedicated to collecting attenuation data.

Because the attenuation detector 18 is dedicated to the attenuation measurement, the requirements for the attenuation detector 18 are different from those for the imaging detectors 14. The attenuation detector 18 of the preferred embodiment consists of a single crystal of dense, fast material such as Lutetium Oxyorthosilicate (LSO) coupled to a single photomultiplier 38. However, it will be understood that other scintillator materials may be used as the material of manufacture of the attenuation detector IS as required. Because the attenuation detector 18 is provided only for detecting events from the point source 12, good energy resolution is not of great importance. Further, because the attenuation detector 18 is positioned proximate the point source 12, the attenuation detector 18 is selected to exhibit low dead-time losses. The attenuation detector 18 and collimator 24 are designed to illuminate only a strip of the imaging detector 14, thereby eliminating events not of interest in the attenuation measurement. As a result of the coincident measurement allowing for electronic collimation, attenuation measurements may be made in the presence of other radiation such as that from a pre-injected patient. Further, the electronic collimation allows for the use of multiple point sources 12, thereby reducing the activity requirements on a single source 12.

Figure 2A:
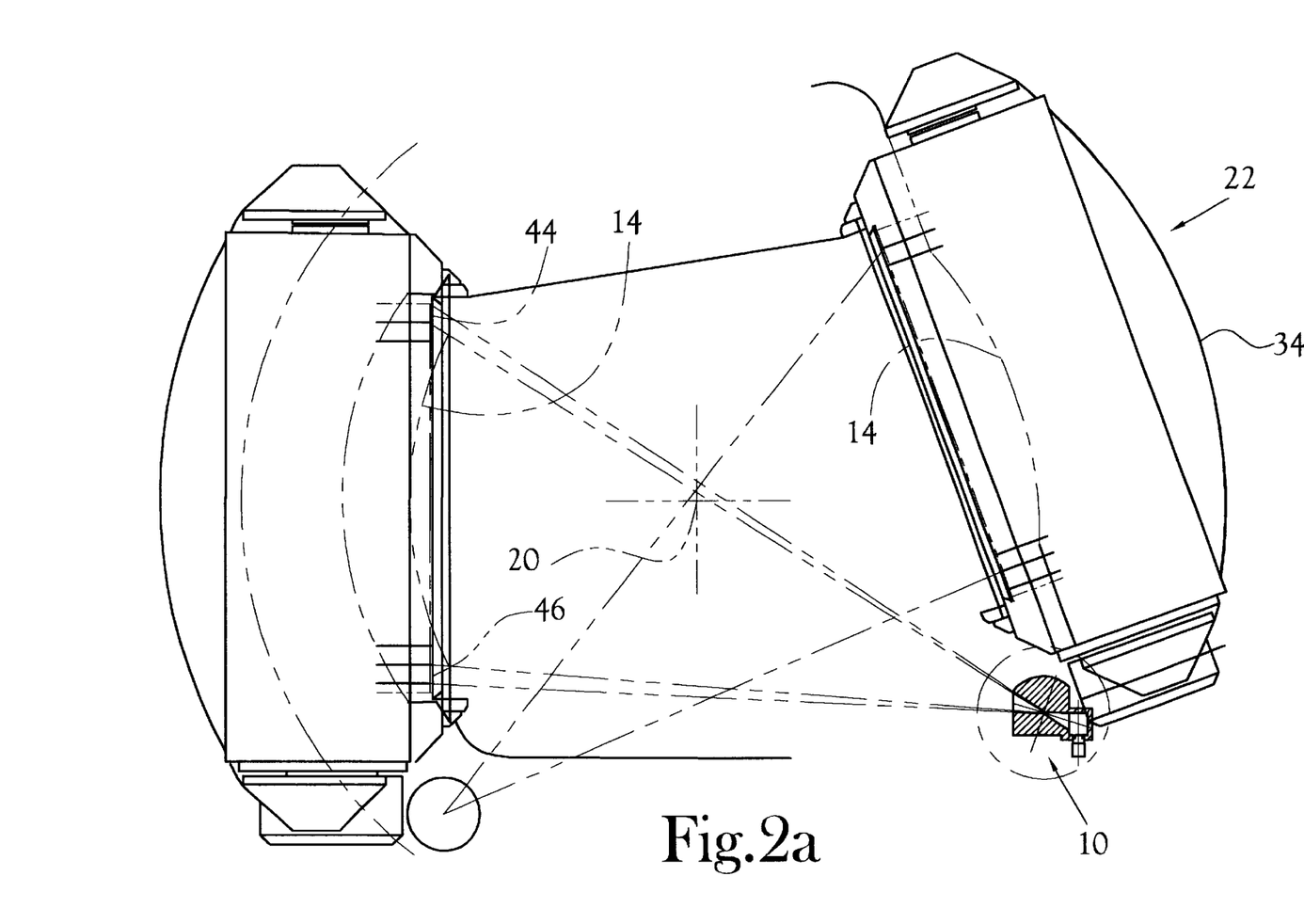
FIG. 2a illustrates an end elevation view, in section, of the transmission source of FIG. 1 showing the point source and detector positioned relative to a two head camera.

FIG. 2A illustrates a device 10 of the present invention disposed opposite each bank of imaging detectors 14 of a dual head camera 22. It will be understood that while a two head gantry is shown, the present invention can be practiced on gantries having any plurality of heads. It will also be understood by those skilled in the art that, in SPECT mode, the heads, in a dual head system, may be opposed from each other at an angle in a range of approximately 90° to approximately 180°. In the preferred embodiment, each device 10 contains four point sources 12 arranged along the axial extent. The sources 10 and the associated source collimators 24 are positioned to the side of each head 34. Because it is preferred that the radiation beam from the point source 12 illuminate the center point 20 of the patient opening 35 (see also FIG. 3), each device 10 is positioned at a slight angle relative to the respective head. As illustrated, the sources 10 and detectors are fixed relative to the imaging heads 34. In order to obtain full coverage of the FOV 16 in the same manner as for an emission scan, the heads and sources 10 are rotated about the center point 20.

Figure 3:
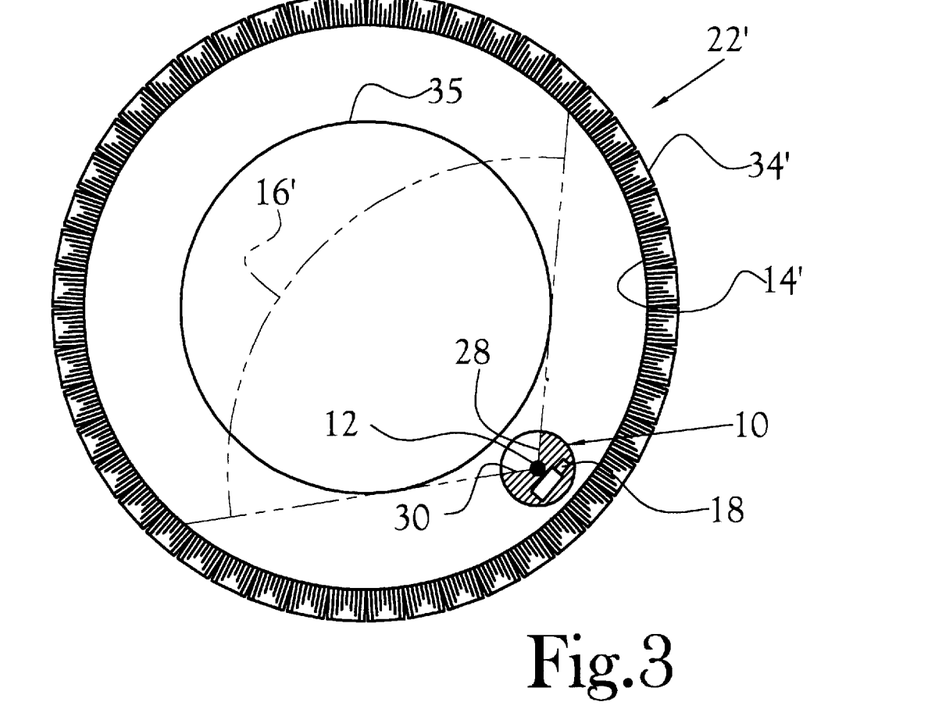
FIG. 3 illustrates an end elevation view, in section, of the transmission source of the present invention showing the point source and detector positioned within a full ring detector.

As illustrated in FIG. 3, the device 10 of the present invention may also be used in association with a full-ring tomograph 22'. In this environment, the device 10 is disposed between the imaging detector ring 34' and the patient opening 35 so as not to interfere with the placement of the patient. In this embodiment, the device 10 is movable within the tomograph 22' in a conventional manner in order to collect attenuation data from each of the plurality of imaging detectors 14'.

Figure 4:
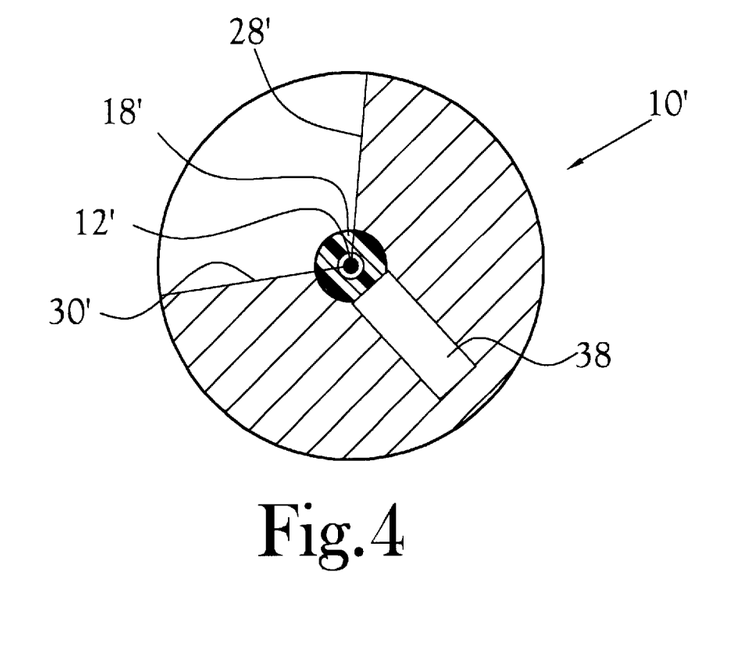
FIG. 4 illustrates an end elevation view, in section, of the transmission source showing the point source encapsulated within a scintillator.

FIG. 4 illustrates an alternate embodiment of the device 10' whereby the point source 12' is encased within a plastic scintillator 18' provided for detecting ionizing radiation, such as, but not limited to beta rays, emitted from the point source 12'. A photomultiplier 38 is disposed behind the point source 12' relative to the viewable imaging detectors 14'. It will be seen by those skilled in the art that other constructions of the present invention may be accomplished whereby an attenuation detector 18 is dedicated solely to the collection of attenuation data from an attenuation point source 12.

Figure 2B:
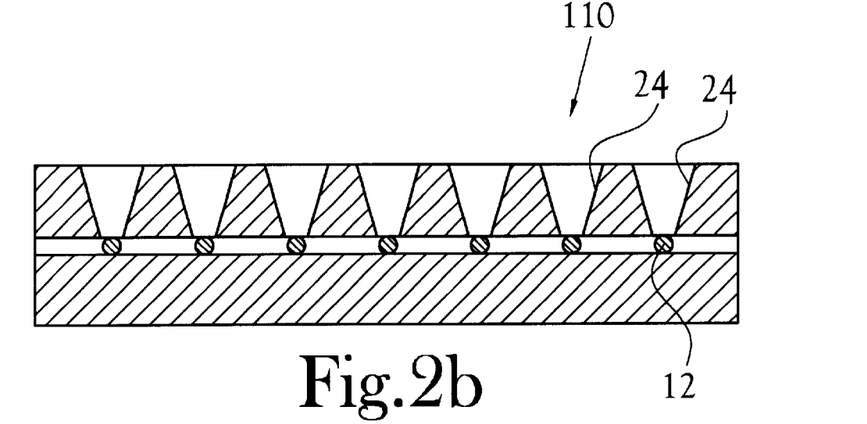
FIGS. 2b–e illustrate cross-sectional views of alternate embodiments of a radiation source that can be utilized in accordance with the present invention.
Figure 2C:
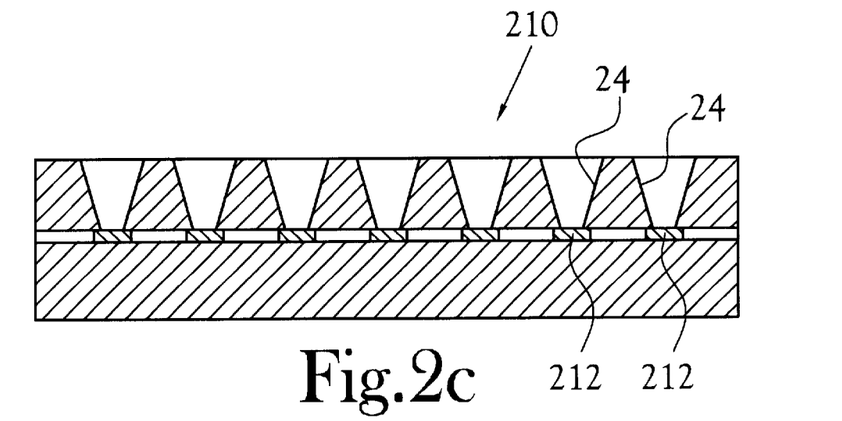
Figure 2D:
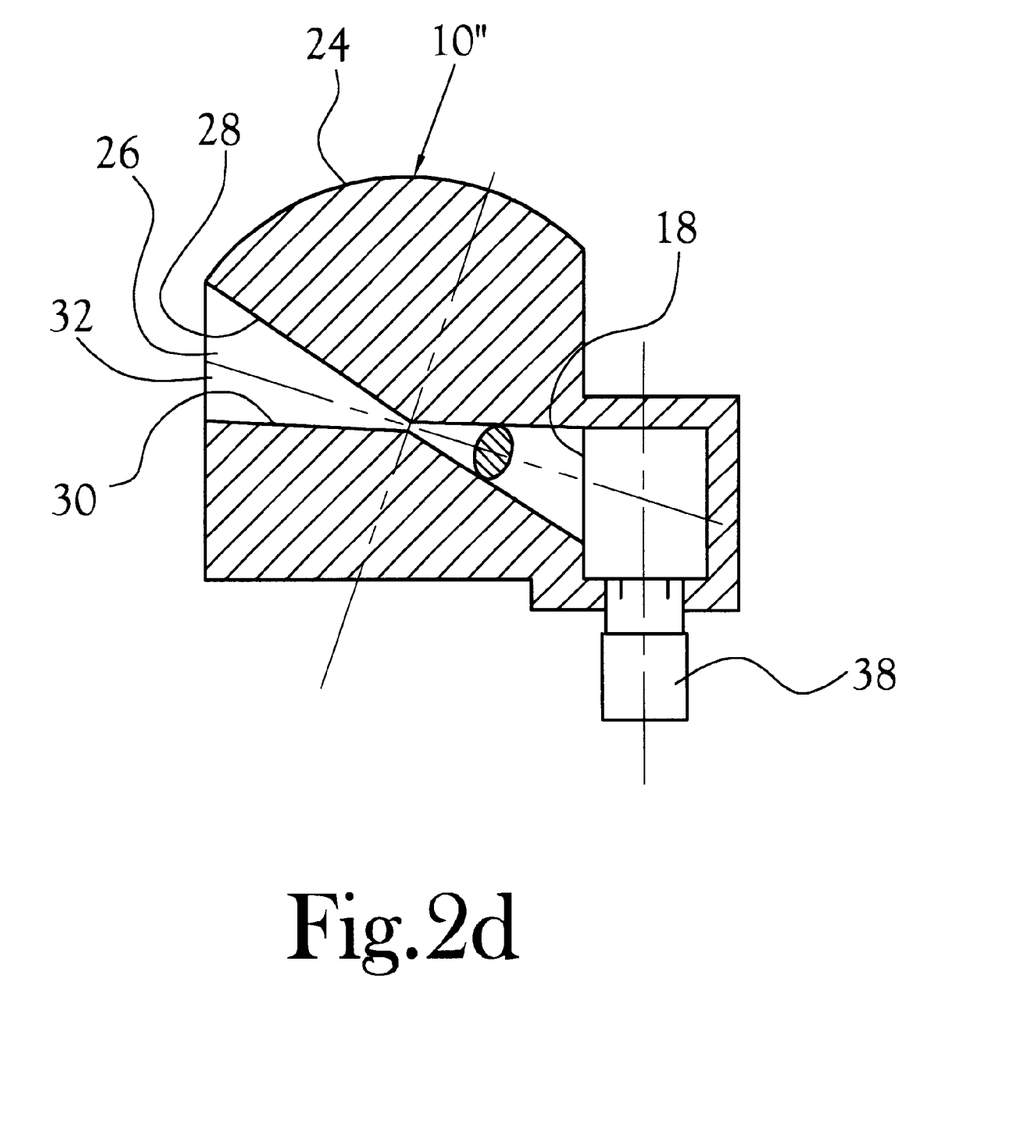
Figure 2E:
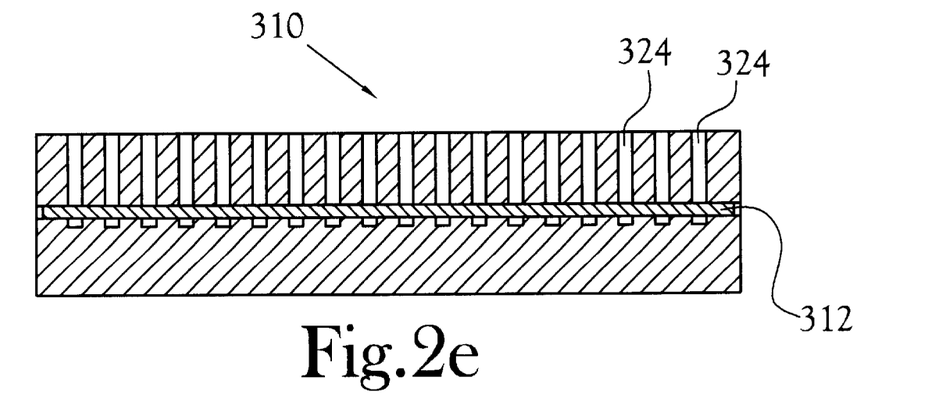

It will be appreciated that while the preferred embodiment utilizes a collimated point source, as illustrated in FIG. 2A, other configurations of radiation sources could also be utilized. In this regard, while device 10 utilizes a single collimated point source 12, as illustrated in FIG. 2b, device 110 is a cylindrical device that incorporates a plurality of collimated point sources 12, in which the collimators 24 are configured as described above, and in which each collimator 24 is positioned to illuminate discrete strips of the imaging detector 14. Illustrated in FIG. 2c is another alternate embodiment of a radiation source. In this regard, device 210 is a cylindrical device that incorporates a plurality of collimated rod sources 212. As described in connection with FIG. 2b, collimators 24 are positioned to illuminate discrete strips of the imaging detector 14. As illustrated in FIG. 2d, device 10" utilizes a flood source 12" rather than a point source 12. And, in FIG. 2e, device 310 is cylindrical and utilizes an elongated rod source 312. Rather than collimators 24, energy from line source 312 is focused on discrete strips of imaging detector 14 by means of a plurality of slits 324 disposed in device 310. It will, of course, be understood that the Figures are for illustrative purposes only and are not drawn to scale. It will also be understood that whereas a plurality of line sources are shown in FIG. 2c, an elongated rod source such as rod source 312 could be utilized in device 210. It will also be understood that other transmission sources, such as moving point sources, helical scan sources or raster scan sources, for example, could be utilized. Further, while the transmission source is illustrated as being attached to an imaging detector, those skilled in the art will appreciate that device 10, 10', 10", 110, 210 or 310 could be detached from an imaging detector. Moreover, as will be recognized by those skilled in the art, when device 10, or one of the alternate embodiments, is used in SPECT mode, attenuation detector 18 is not utilized.

Figure 5:
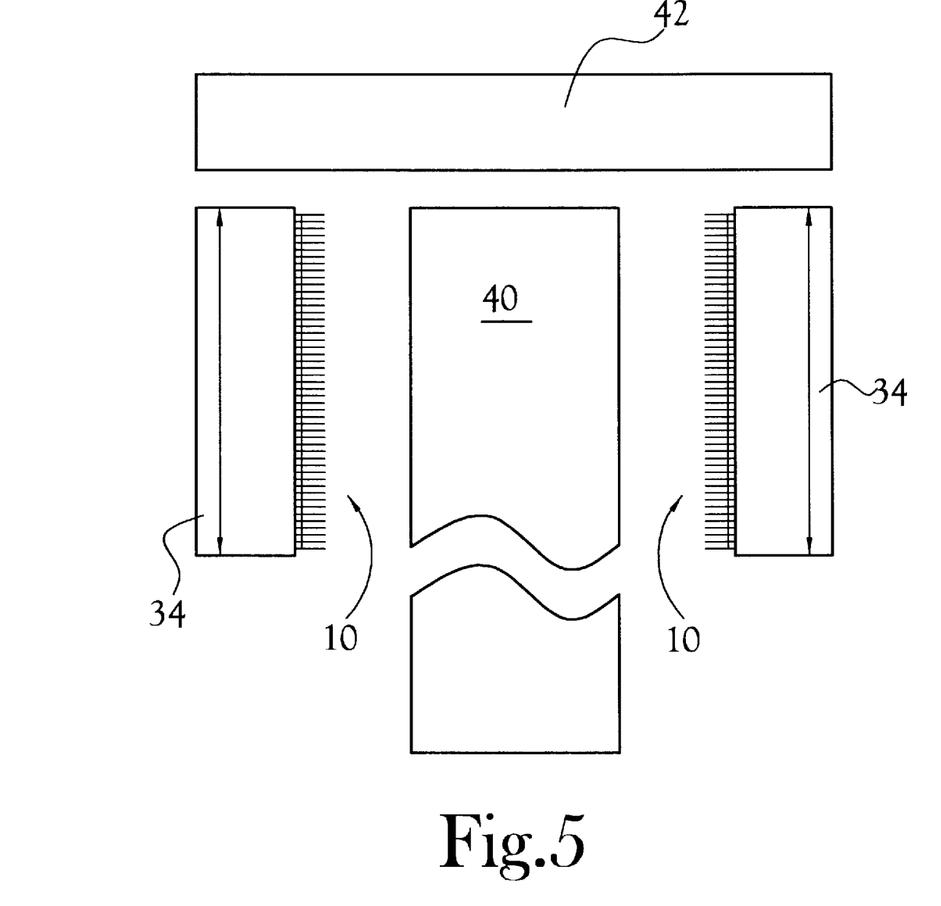
FIG. 5 illustrates a top plan view of a dual head tomograph incorporating two banks of collimated point sources made in accordance with several features of the present invention.
Figure 6:
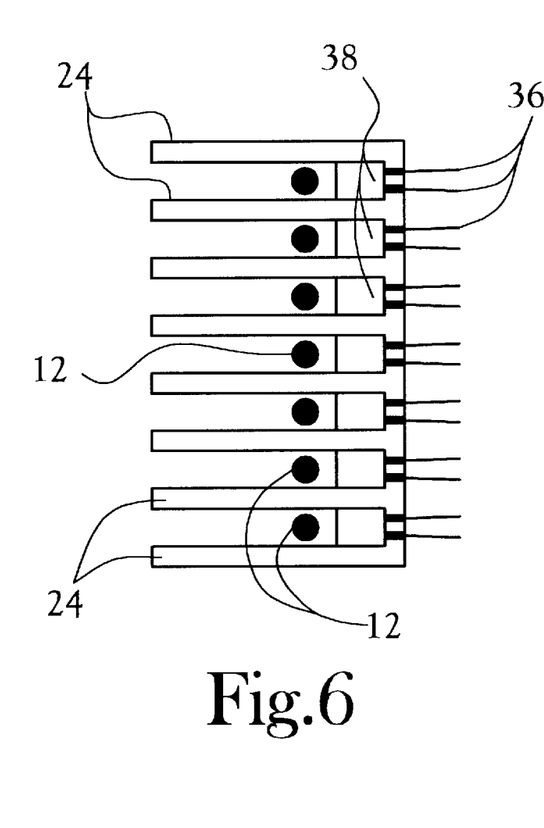
FIG. 6 illustrates an enlarged portion of a collimator showing an arrangement between a plurality of point sources, a similar plurality of dedicated gamma radiation detectors, and corresponding pairs of fiber optic cables.

FIG. 5 illustrates the top plan view of a dual head tomograph 22 device having two banks of collimated point sources 12 positioned in reference to a patient bed 40 and a gantry 42. FIG. 6 is an enlarged view of a portion of one bank of the collimated point sources 12. One point source 12 is disposed between successive pairs of collimators 24 and immediately in front of one dedicated gamma radiation detector 18. However, it will be understood by those skilled in the art that a single source 12 of radiation may define a rod-shaped configuration and extend behind or through the collimators 24 and thus successfully serve as the plurality of point sources 12. Each detector 18 is provided for detecting 511 keV gamma radiation which does cross the tomographic field of view. Two groups of fiber optic cables 36 are connected at a proximal end to each detector 18, with the exception of a few detectors 18 to be described below which only have one fiber optic cable 36 connected thereto. The distal end of each fiber optic cable 36 is connected to an optical detector such as a photomultiplier tube (PMT) 38, as more clearly illustrated in FIG. 7.

Figure 7:
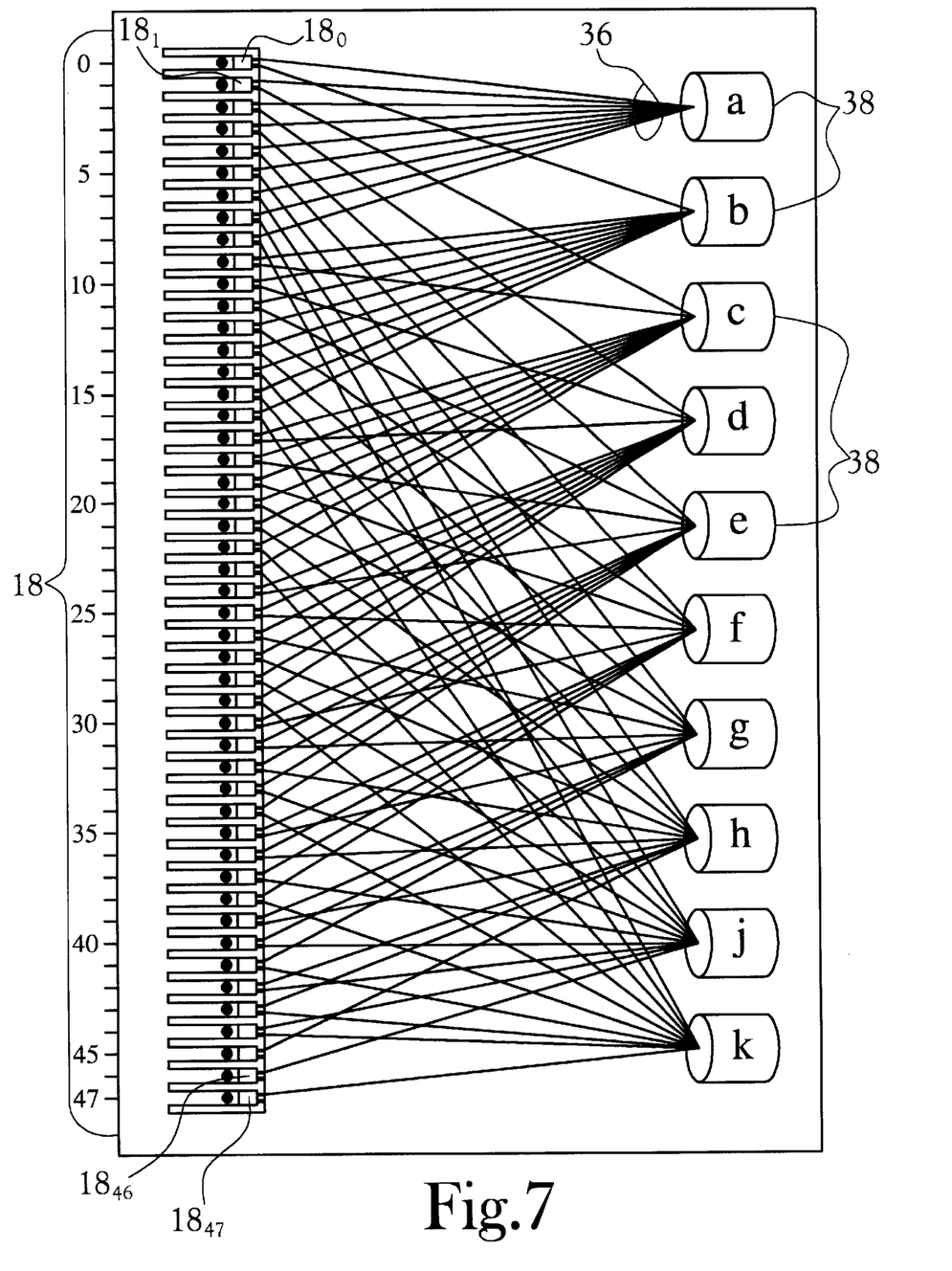
FIG. 7 is a schematic diagram representing a portion of the fiber optic connections between the dedicated gamma radiation detectors and the photomultiplier tubes.

Illustrated in FIG. 7 are 48 detectors $18_{0-47}$, interconnected to ten (10) PMT's 38a–k. The fiber optic cables 36 interconnected between the detectors $18_{0-47}$ and the PMT's 38a–k are arranged such that no two fiber optic cables 36 are connected between the same detector 18 and the same PMT 38. Using the convention described above, Table 1 below more clearly illustrates the fiber optic connections.

TABLE 1

|   | b | c | d | e | f | g | h | j | k |
|---|---|---|---|---|---|---|---|---|---|
| a | 0 | 1 | 2 | 3 | 4 | 5 | 6 | 7 | 8 |
| b |   | 9 | 10 | 11 | 12 | 13 | 14 | 15 | 16 |
| c |   |   | 17 | 18 | 19 | 20 | 21 | 22 | 23 |
| d |   |   |   | 24 | 25 | 26 | 27 | 28 | 29 |
| e |   |   |   |   | 30 | 31 | 32 | 33 | 34 |
| f |   |   |   |   |   | 35 | 36 | 37 | 38 |
| g |   |   |   |   |   |   | 39 | 40 | 41 |
| h |   |   |   |   |   |   |   | 42 | 43 |
| j |   |   |   |   |   |   |   |   | 44 |
|   |   |   |   |   |   |   | 45 | 46 | 47 |

In this table, a through k are the PMT 38 labels and 0 through 47 are the detector 18 labels. It will be seen from the FIG. 7 and from the above table that PMT's 38a–g are optically coupled with nine (9) detectors 18 each while PMT's 38h, 38j and 38k are optically coupled with ten (10) detectors 18 each. Further, it will be seen that detectors $18_{0-44}$ are optically coupled with two (2) PMT's 38 each, while detectors $18_{45-47}$ are optically coupled with one (1) PMT 38 each. Of course, it will be understood that other configurations may be adopted as well and with similar results. Coincidence detection of pulse output from unique pairs of PMT's 38, or a single detection in PMT's 38h, 38j or 38k, determines which detector 18 received the near-side gamma radiation from its respective point source 12. The lengths of each optical fiber 36 in a fiber optic pair are equal in order to ensure that pulse output at the corresponding PMT's 38 is simultaneous.

Figure 8:
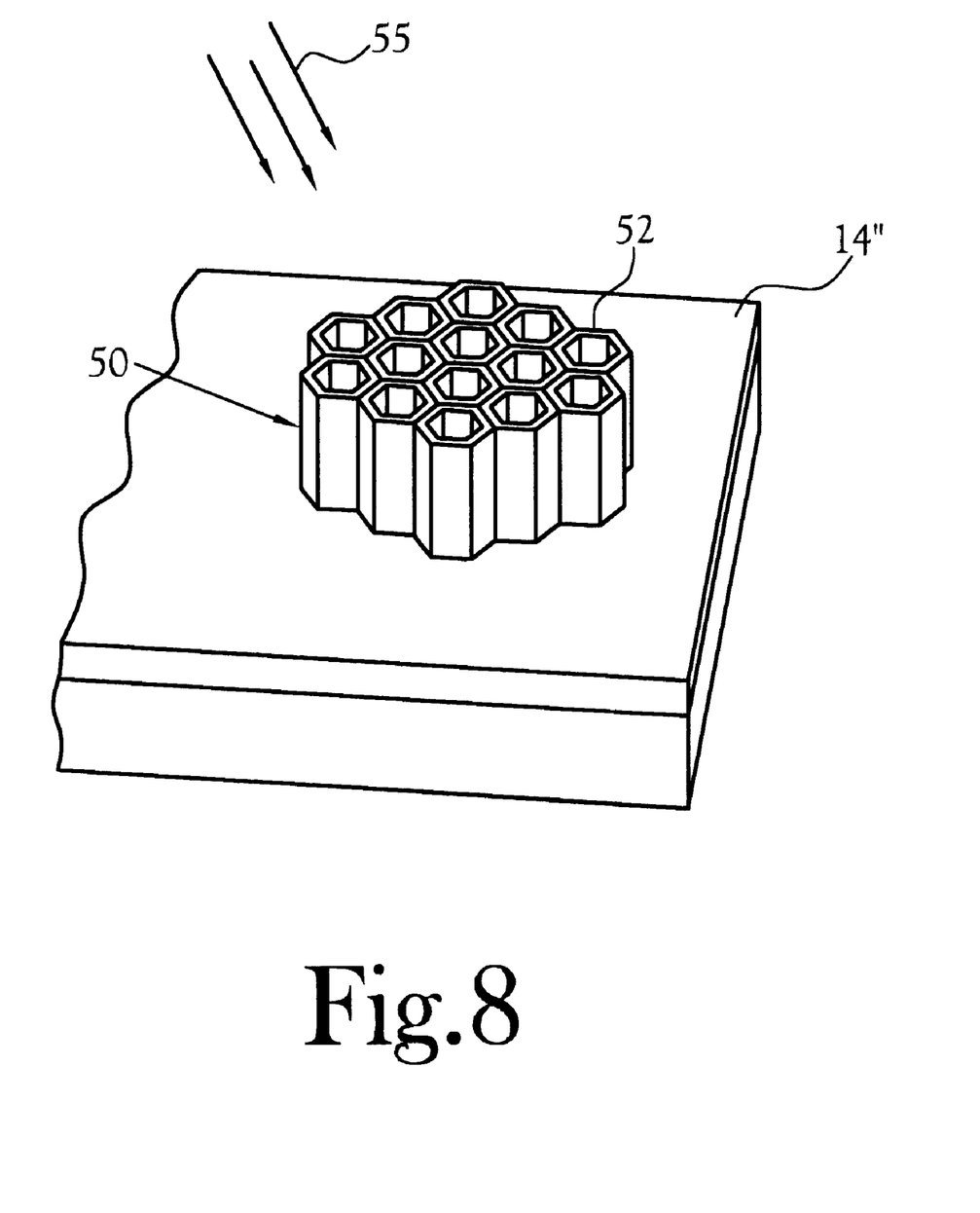
FIG. 8 is a schematic view of a SPECT detector and associated parallel hole collimators.

In SPECT mode, an imaging collimator 50 will be attached to the imaging detector 14" to collimate the gamma photons emitted from the subject, as is understood by those skilled in the art. As recognized by those skilled in the art, the imaging collimator 50 may have a number of forms. In this regard, a typical embodiment consists of a grid of hexagonally arranged holes approximately 1–2 mm in diameter and 25 mm in height. The septa 52 is usually made of lead. The septa 52 are approximately 0.2–0.3 mm thick and are designed for low energy gamma photons, i.e. photons of less than 170 keV, and preferably in a range between 140 keV and 170 keV. If collimators designed for gamma photon energies above 170 keV are selected, a higher energy point source must also be selected, since such high energy collimators also have a significantly greater collimator attenuation. To avoid the necessity of orienting the transmission source 12 at the focal point(s) of the imaging collimator 50, as is the case with existing methods, the transmission source 12 is oriented so as to be oblique to the collimator septa 52. The point source 12, or any of the alternate embodiments described above, is selected to be of sufficiently high energy and flux density in order to allow transmission measurements to be taken through the subject and, additionally, through the imaging collimator septa 52. In this regard, preferred sources of radiation include Cs-137 and I-131. Those skilled in the art will recognize that other, comparably high energy sources can be used as well. It will be recognized by those skilled in the art that collimators can also have one of a number of focal orientations. While the preferred collimator 50 for this embodiment is a parallel hole collimator, other classical collimator forms, such as fan beam, asymmetric fan beam, cone beam, slant hole, and slat collimators are also acceptable for the present invention.

As discussed above, the transmission source 12 is collimated at the source and focused towards the detector 14". The gamma photons from the transmission source 12 traverse through the subject and the surviving photons impinge upon the detector collimator 50 at an oblique angle represented by arrows 55. A portion of these photons penetrate through the collimator septa 52 and are detected. Taking a series of measurements from around the subject comprises a tomographic dataset suitable for reconstruction of the subject attenuation map. To make the attenuation reconstruction problem tractable, the transmission gamma photon energy and point of origin are both known—additional collimation at the detector is not required. During SPECT emission reconstruction, this map will be used to compensate for emission photon attenuation. The technique is particularly useful for compensating deep structures and is a necessary part of quantification of emission activity. State of the art iterative reconstruction algorithms are acceptable for performing image reconstruction with attenuation correction.

Figure 9:
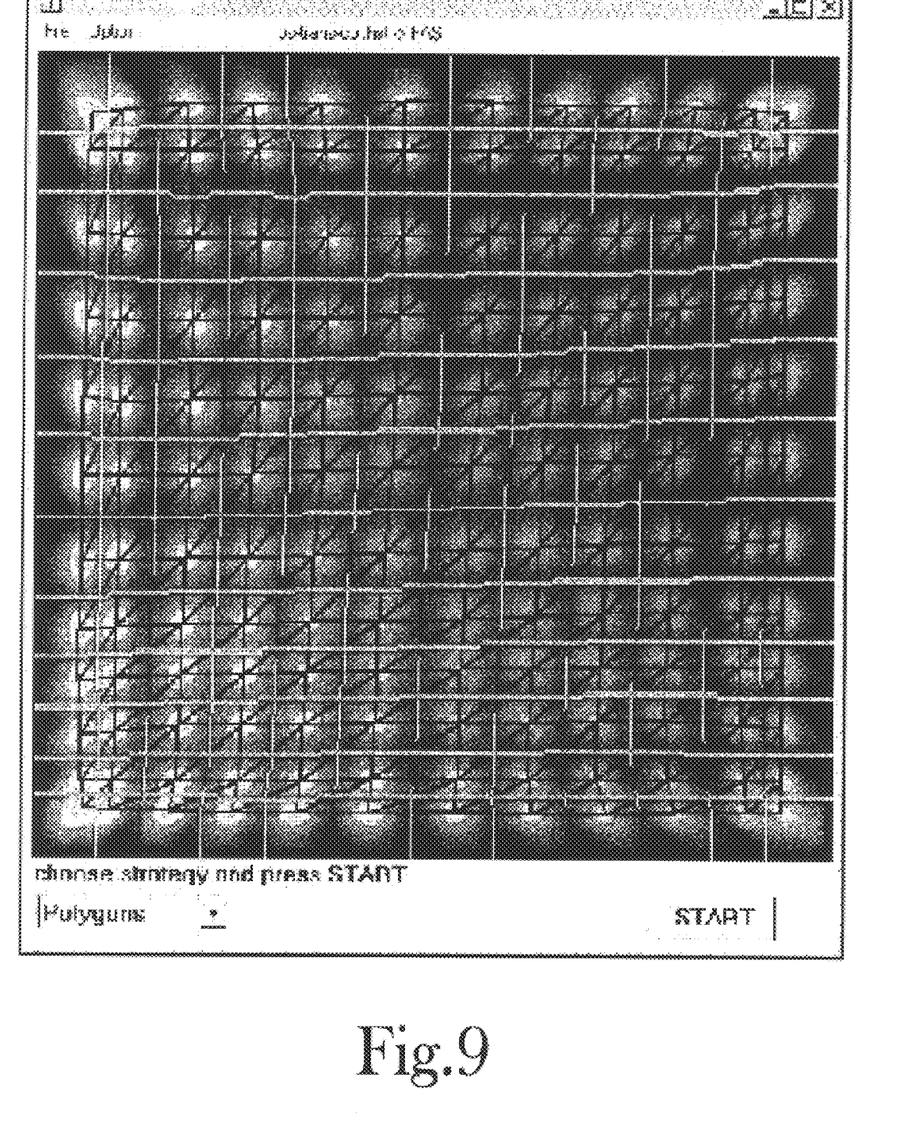
FIG. 9 is a histogram showing measurements of crystal responses for a collimator section with a discrete detector scanned in accordance with the teachings of the alternate embodiment.
Figure 10:
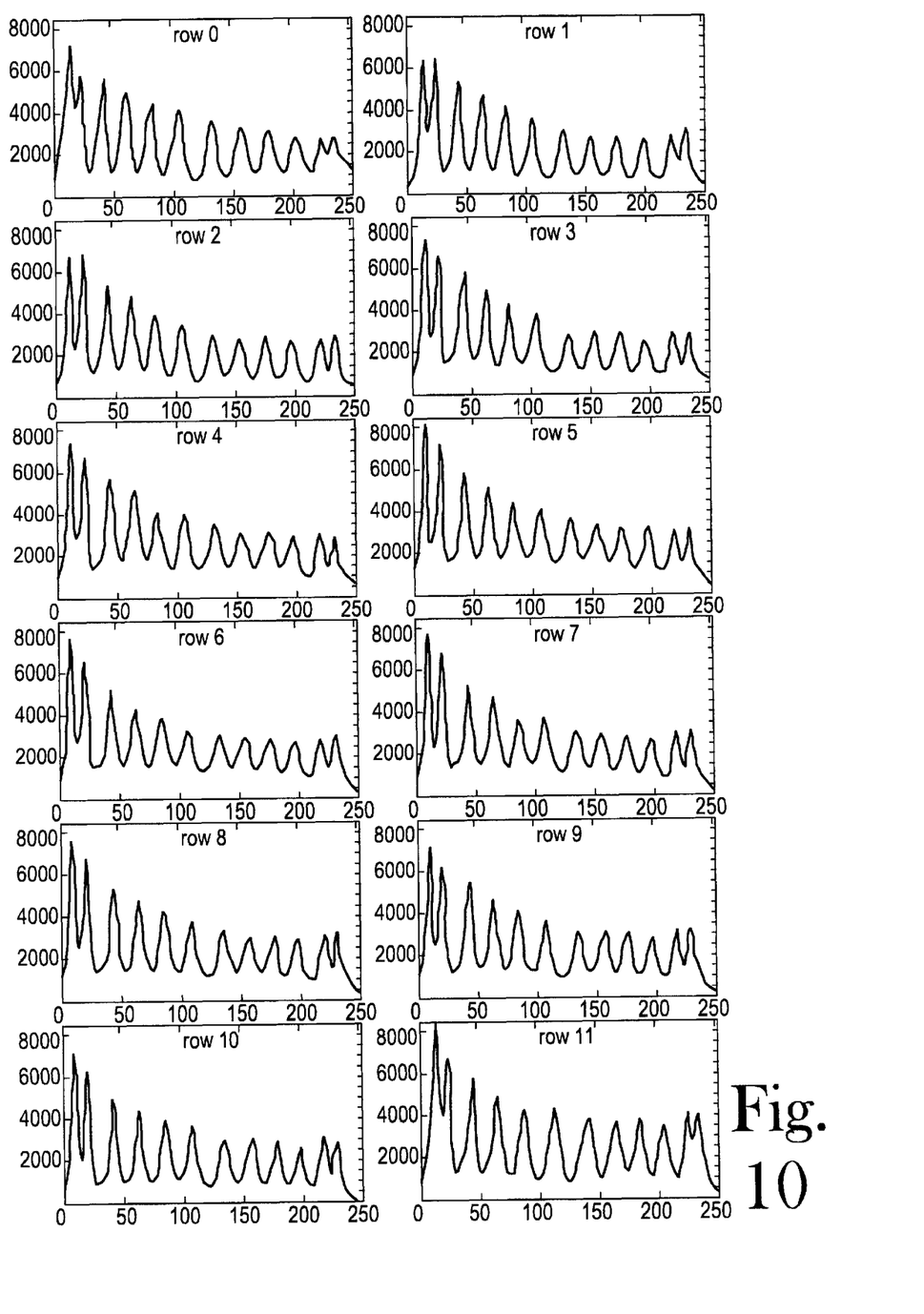
FIG. 10 represents the one dimensional cross sectional views of crystal row responses for the image shown in FIG. 9.

Since the transmission source 12 is offset and oblique to the collimator 50, the gamma photon beam sweeps out a range of intercept angles with the collimator septa. This results in a continuously varying attenuation path through the collimator 50. The more perpendicular the beam to the detector 14, when using parallel hole collimators, the less overall attenuation the gamma beam will experience. To illustrate this concept, measurements for a collimator section with a discrete detector are shown in FIGS. 9 and 10. The detector used in FIGS. 9 and 10 consists of a block of scintillating material cut into individual crystals in a 12×12 array approximately 5 cm×5 cm on a side. Those skilled in the art will recognize that there are a number of detector technologies available for PET and SPECT applications and that this detector arrangement is used merely as an example. In the case illustrated in FIGS. 9 and 10, the transmission source was oriented on the left side of the block, as indicated by the brighter pixels, in FIG. 9, on the left. Also, it is noted that activity can be observed in all block regions. Illustrated in FIG. 10 are one dimensional cross sectional views of crystal row responses for the image shown in FIG. 9. Note that twelve distinct crystals are indicated by the approximately gaussian peaks. Also noted is the exponential fall off of peak magnitude due to the increasing gamma path length through the lead septa. As will be recognized by those skilled in the art, nonlinear correction has to be applied to the data to compensate for the increased path length through the collimator as the transmission angle becomes more oblique.

While this embodiment has been described with a preferred transmission source 12 oriented at 158 degrees, it will be recognized that other alternate transmission source implementations/orientations are suitable to the present invention. For instance, it will be recognized that point sources, either coincidence or singles, tightly collimated line sources, and collimated flood sources could be utilized. Also, while the transmission source of the present invention is taught as being attached to the detector gantry, it will be recognized that the transmission source could be distinct and separate from the detector gantry. Also, while a flat detector 14 has been illustrated, a curved crystal could be used for the detector resulting in fewer septa crossings, and less attenuation, and ability to use a more compact transmission source location in order to keep the center of rotation in the FOV. It will be recognized that the present invention for attenuation correction is useful for acquiring transmission and emission data simultaneously thus allowing for simultaneous PET/SPECT.

From the foregoing description, it will be recognized by those skilled in the art that a transmission source offering advantages over the prior art has been provided. Specifically, the transmission source is provided for detecting activity from a collimated point source for performing transmission attenuation correction. Moreover, the source of the present invention includes a detector dedicated to collecting attenuation data, thus changing the physical requirements of the attenuation detector as compared to an imaging detector and permitting it to be designed to achieve much lower dead time than a standard imaging detector. The collimated point source and dedicated detector are positioned with respect to the tomography device such the only a selected strip of the imaging detector is illuminated such that events unrelated to the attenuation are eliminated. Further, when used in SPECT mode, the transmission source has a high enough energy and flux density to shine through the imaging collimators used in conjunction with the imaging detectors.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention,
We claim:

1. A transmission source for accomplishing attenuation data collection relative to activity from a radiation source associated with a tomograph device having at least one imaging detector positioned to define a field of view, said transmission source comprising:
   a radiation source positioned with respect to the tomograph device such that gamma radiation therefrom illuminates at least one imaging detector on the tomograph device; and
   an attenuation detector for collecting attenuation data relative to said radiation source in time coincidence with data collected by each imaging detector, said attenuation detector being independent from the at least one imaging detector, said attenuation detector being fabricated from Lutetium Oxyorthosilicate (LSO) coupled to a single photomultiplier.

2. The transmission source of claim 1 further comprising an attenuation collimator positioned with respect to the tomograph device such that a selected portion of the at least one imaging detector of the tomograph device is illuminated by said radiation source, thereby eliminating events unrelated to said attenuation data, said attenuation collimator defining an opening for exposing said radiation source to the selected portion of the at least one imaging detector of the tomograph device, said opening defining a top shield wall and a bottom shield wall, said top shield wall extending from said radiation source toward a far portion of the at least one imaging detector opposite said transmission source, said bottom shield wall extending toward a near portion of the at least one imaging detector opposite said transmission source, said opening further defining a pair of side shield walls spaced apart limit a width of a collimated radiation beam emitted from said radiation source toward the selected portion of the at least one imaging detector.

3. The transmission source of claim 1 wherein said imaging detector includes an imaging collimator, said imaging collimator having septa and wherein said radiation source is selected to have an energy and flux density sufficient to allow transmission measurements to be taken through a subject and through said imaging collimator septa.

4. The transmission source of claim 3 wherein transmission source is used for collecting attenuation data for simultaneous acquisition of transmission and emission data.

5. The transmission source of claim 2 wherein said attenuation detector is disposed within said attenuation collimator behind said radiation source relative to the tomograph device imaging detector.

6. The transmission source of claim 2 wherein said attenuation detector is disposed within said attenuation collimator and encapsulates said radiation source relative to the tomograph device imaging detector, said attenuation detector being provided for detecting ionizing radiation emitted from said radiation source.

7. The transmission source of claim 1 wherein said attenuation detector is selected to exhibit high sensitivity and low dead-time losses.

8. The transmission source of claim 1 wherein said radiation source is fixed relative to the imaging detector of the tomograph device, said transmission source and the imaging detector being rotated about a center of the tomograph device in order to obtain full coverage of the field of view (FOV) of the tomograph device.

9. The transmission source of claim 1 adapted for use in a tomograph device having dual imaging heads, each imaging head having at least one imaging detector, said transmission source including two of said radiation source and two of said attenuation detector, with one each of said radiation source and said attenuation detector disposed across from each imaging head such that a selected portion of the at least one imaging detector of the imaging head is illuminated thereby.

10. The transmission source of claim 1 comprising a plurality of said attenuation detector, said transmission source further comprising a plurality of optical detectors, each of said plurality of attenuation detectors being optically coupled to at least one of said plurality of optical detectors, each of said plurality of optical detectors being optically coupled to a subset of said plurality of said attenuation detectors, said plurality of optical detectors being less than said plurality of attenuation detectors.

11. The transmission source of claim 1 wherein said transmission source is a coincidence transmission source.

12. The transmission source of claim 1 wherein said transmission source is a singles transmission source.

13. A singles transmission source for accomplishing attenuation data collection relative to activity from a radiation source associated with a tomograph device having at least one imaging detector and an associated imaging collimator, said imaging collimator having septa positioned to define a field of view, said transmission source comprising:

a radiation source positioned with respect to the tomography device such that gamma radiation therefrom illuminates at least one imaging detector on the tomography device, wherein said radiation source is selected to have an energy and flux density sufficient to allow transmission measurements to be taken through a subject and through said imaging collimator septa.

14. A transmission source for accomplishing attenuation data collection relative to activity from a radiation source associated with a tomograph device having at least one imaging detector positioned to define a field of view, said transmission source comprising:

a radiation source positioned with respect to the tomograph device such that gamma radiation therefrom illuminates at least one imaging detector on the tomograph device;

a plurality of attenuation detectors for collecting attenuation data relative to said radiation source in time coincidence with data collected by each imaging detector, said attenuation detector being independent from the at least one imaging detector; and a plurality of optical detectors, each of said plurality of attenuation detectors being optically coupled to at least one of said plurality of optical detectors, each of said plurality of optical detectors being optically coupled to a subset of said plurality of said attenuation detectors, said plurality of optical detectors being less than said plurality of attenuation detectors.

15. The transmission source of claim 14, further comprising an attenuation collimator positioned with respect to the tomograph device such that a selected portion of the at least one imaging detector of the tomograph device is illuminated by said radiation source, thereby eliminating events unrelated to said attenuation data, said attenuation collimator defining an opening for exposing said radiation source to the selected portion of the at least one imaging detector of the tomograph device, said opening defining a top shield wall and a bottom shield wall, said top shield wall extending from said radiation source toward a far portion of the at least one imaging detector opposite said transmission source, said bottom shield wall extending toward a near portion of the at least one imaging detector opposite said transmission source, said opening further defining a pair of side shield walls spaced apart to limit a width of a collimated radiation beam emitted from said radiation source toward the selected portion of the at least one imaging detector.

16. The transmission source of claim 14, wherein said imaging detector includes an imaging collimator, said imaging collimator having septa and wherein said radiation source is selected to have an energy and flux density sufficient to allow transmission measurements to be taken through a subject and through said imaging collimator septa.

17. The transmission source of claim 16 wherein transmission source is used for collecting attenuation data for simultaneous acquisition of transmission and emission data.

18. The transmission source of claim 15, wherein said attenuation detector is disposed within said attenuation collimator behind said radiation source relative to the tomograph device imaging detector.

19. The transmission source of claim 15, wherein said attenuation detector is disposed within said attenuation collimator and encapsulates said radiation source relative to the tomograph device imaging detector, said attenuation detector being provided for detecting ionizing radiation emitted from said radiation source.

20. The transmission source of claim 14 wherein said attenuation detector is fabricated from a scintillation material which exhibits fast response times.

21. The transmission source of claim 20 wherein said attenuation detector is fabricated from Lutetium Oxyorthosilicate (LSO) coupled to a single photomultiplier.

22. The transmission source of claim 14 wherein said attenuation detector is selected to exhibit high sensitivity and low dead-time losses.

23. The transmission source of claim 14 wherein said radiation source is fixed relative to the imaging detector of the tomograph device, said transmission source and the imaging detector being rotated about a center of the tomograph device in order to obtain full coverage of the field of view (FOV) of the tomograph device.

24. The transmission source of claim 14 adapted for use in a tomograph device having dual imaging heads, each imaging head having at least one imaging detector, said transmission source including two of said radiation source and two of said attenuation detector, with one each of said radiation source and said attenuation detector disposed across from each imaging head such that a selected portion of the at least one imaging detector of the imaging head is illuminated thereby.

25. The transmission source of claim 16 wherein said imaging collimator is adapted for low energy gamma photons having less than approximately 170 keV.

26. The transmission source of claim 14 wherein said transmission source is a coincidence transmission source.

27. The transmission source of claim 14 wherein said transmission source is a singles transmission source.

* * * * *